United States Patent
Shepard

(10) Patent No.: US 7,998,206 B2
(45) Date of Patent: Aug. 16, 2011

(54) OSTEOCHONDRAL CORE CENTRIFUGATION SYSTEM AND METHOD OF OSTEOCHONDRAL REPAIR

(75) Inventor: David O. Shepard, Naples, FL (US)

(73) Assignee: Arthrex, Inc., Naples, FL (US)

( * ) Notice: Subject to any disclaimer, the term of this patent is extended or adjusted under 35 U.S.C. 154(b) by 642 days.

(21) Appl. No.: 11/369,962

(22) Filed: Mar. 8, 2006

(65) Prior Publication Data

US 2006/0205076 A1    Sep. 14, 2006

Related U.S. Application Data

(60) Provisional application No. 60/659,435, filed on Mar. 9, 2005.

(51) Int. Cl.
*A61F 2/28* (2006.01)
*A61L 2/00* (2006.01)

(52) U.S. Cl. .................. 623/16.11; 422/28; 422/532

(58) Field of Classification Search ............... 623/16.11; 422/28, 532; 435/40.5
See application file for complete search history.

(56) References Cited

U.S. PATENT DOCUMENTS

| 5,919,196 | A * | 7/1999 | Bobic et al. .................. 606/86 |
| 5,977,432 | A | 11/1999 | Wolfinbarger, Jr. et al. |
| 6,231,608 | B1 | 5/2001 | Stone |
| 6,547,794 | B2 * | 4/2003 | Auge', II .................. 606/86 R |
| 2001/0012965 | A1 | 8/2001 | Masuda et al. |
| 2004/0033212 | A1 | 2/2004 | Thomson et al. |
| 2004/0219058 | A1 | 11/2004 | Shimp et al. |
| 2004/0230303 | A1 | 11/2004 | Gomes et al. |

FOREIGN PATENT DOCUMENTS

CN            1569249        *   1/2005

* cited by examiner

*Primary Examiner* — Maria Leavitt
(74) *Attorney, Agent, or Firm* — Dickstein Shapiro LLP

(57) ABSTRACT

An osteochondral centrifugation system for providing an osteochondral centrifuged core from a graft such as femoral condyle, for example. The centrifugation system may be used either in the operating room or, alternatively, at a tissue banking facility at the time of processing. The osteochondral centrifuged core is formed by (i) removing an osteochondral core from a graft; (ii) placing the osteochondral core in a centrifugation system to remove blood, lipids, or other potentially antigenic or contaminating materials, and to obtain a centrifuged core; and (iii) optionally, subjecting the centrifuged core to a material that reduces the chance of disease transmission and aids in the healing of the recipient site to which the centrifuged core is to be transferred.

11 Claims, 5 Drawing Sheets

OSTEOCHONDRAL CORE CENTRIFUGATION SYSTEM AND METHOD OF OSTEOCHONDRAL REPAIR

This application claims the benefit of U.S. Provisional Application Ser. No. 60/659,435, filed on Mar. 9, 2005, the disclosure of which is incorporated by reference herein.

FIELD OF THE INVENTION

The present invention relates to osteochondral cores and, more specifically, to a method and apparatus for providing an osteochondral core that is free of contaminants and/or potentially antigenic materials.

BACKGROUND OF THE INVENTION

Transplantation of arthroscopic osteochondral autograft for repairing chondral defects is known in the art. The transplantation procedure typically involves providing a donor graft osteochondral core (from a selected donor site) and transplanting the osteochondral core into corresponding sized recipient sockets (of a recipient repair site).

Donor sites for osteochondral cores, capped with intact cartilage, are selected prior to notchplasty. If the chondral defect is a femoral one, donor sites are selected along the anterolateral and superior aspect of the notchplasty area, or on the superolateral and anterolateral aspect of the lateral femoral condyle in the non-weightbearing area above the sulcus terminalis. At the donor sites, multiple osteochondral cores 5 mm to 9 mm in diameter and 10 to 15 mm long are harvested using various cutting instruments.

Recipient repair sites typically are located on the weight-bearing area of the medial and lateral femoral condyles. Full-thickness chondral defects, typically larger than 10 mm in diameter, and up to 20 mm, are selected for treatment. Recipient sockets at the repair sites are prepared, and the donor cores are transferred and press-fitted into the recipient sockets.

Although the above-described transplantation procedure works well for various chondral defects, improvements are needed in the formation of the donor cores, especially to facilitate transplant insertion, and to reduce contamination and promote healing of the recipient site.

SUMMARY OF THE INVENTION

The present invention provides an osteochondral centrifugation system for providing an osteochondral core from a graft such as femoral condyle, for example. The centrifugation system may be used either in the operating room or, alternatively, at a remote location (such as a tissue banking facility) at the time of processing.

The present invention also provides a method of processing an osteochondral core from a graft in the operating room. The method comprises the steps of: (i) providing an osteochondral core from a graft in the operating room; (ii) placing the osteochondral core in a centrifugation system in the operating room, to remove blood or potentially antigenic or contaminating materials, and to obtain a centrifuged core; and (iii) optionally, subjecting the centrifuged core to a material that reduces the chance of disease transmission and aids in the healing of the recipient site to which the centrifuged core is to be transferred.

The present invention also provides a method of processing an osteochondral core from a graft at a location remote from the operating room (for example, a tissue banking facility). The method comprises the steps of: (i) providing an osteochondral core from a graft at the remote location; (ii) placing the graft in a centrifugation system at the remote location, to remove blood or potentially antigenic or contaminating materials, and to obtain a centrifuged core; and (iii) optionally, subjecting the centrifuged core to a material that reduces the chance of disease transmission and aids in the healing of the recipient site to which the centrifuged core is to be transferred.

The present invention is also directed to methods of osteochondral repair using preformed centrifuged cores. An exemplary method of the present invention includes the steps of (i) creating a recipient socket; (ii) providing a centrifuged core selected to fit the socket; and (iii) inserting the selected centrifuged core into the recipient socket.

The present invention further provides a centrifuged core formed by the steps of (i) providing an osteochondral core from a graft either in the operating room or at a remote location (for example, a tissue banking facility); (ii) placing the graft in a centrifugation system to remove blood or potentially antigenic or contaminating materials, and to obtain a centrifuged core; and (iii) optionally, infusing the centrifuged core with a material (for example, a solution) that reduces the chance of disease transmission and aids in the healing of the recipient site to which the centrifuged core is to be transferred.

Other features and advantages of the present invention will become apparent from the following description of the invention which refers to the accompanying drawings.

DETAILED DESCRIPTION OF THE INVENTION

Figure 1:
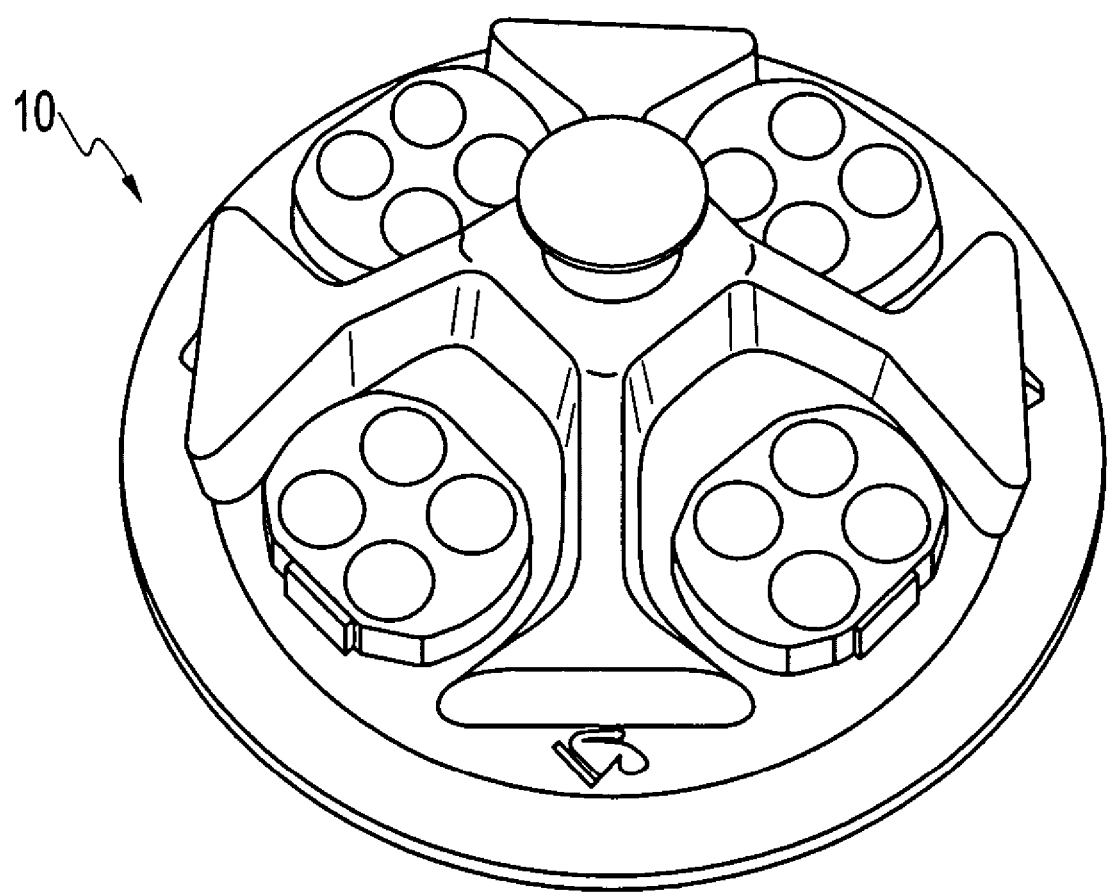
FIG. 1 illustrates a top view of a section of a rotor chamber or centrifugation system for processing osteochondral cores according to a method of the present invention.
Figure 2:
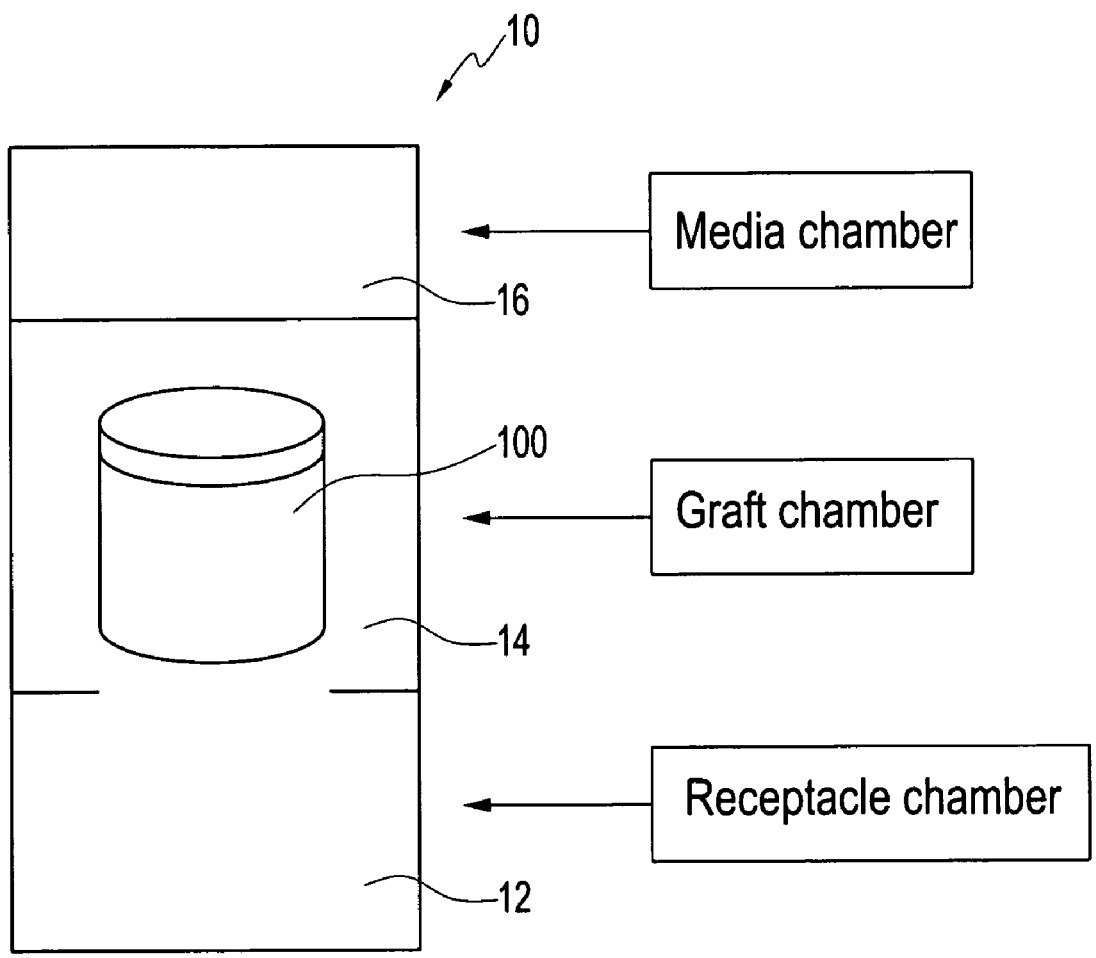
FIG. 2 illustrates a schematic view of a graft chamber according to an embodiment of the present invention.

Referring now to the drawings, where like elements are designated by like reference numerals, a top view of an exemplary centrifugation system 10 of the present invention is shown in FIG. 1. FIG. 2 illustrates the centrifugation system 10 of the present invention comprising a receptacle chamber 12, a graft chamber 14 and an optional media chamber 16. Centrifuged core 100 is formed in the graft chamber 14 according to a method of the present invention and as described below.

The centrifugation system 10 may be used in the operating room or, alternatively, at a remote location (such as a tissue banking facility) at the time of processing.

If the processing takes place in an operating room, an osteochondral core from a graft such as femoral condyle, talus, or humeral head, for example, is first removed by a surgeon from a whole or partial graft (for example, a hemicondyle). The osteochondral core is cleaned in a normal fashion and the cleaned core is subsequently placed in the centrifugation system 10 of FIG. 1. In the centrifuge, the cleaned core is processed to remove blood, lipids, or other potentially antigenic or contaminating materials, and to obtain centrifuged core 100.

Optionally, the centrifuged core 100 may then be infused with a media material that reduces the chance of disease transmission and aids in the healing of the recipient site to which the centrifuged core is to be transferred. In an exemplary embodiment, the media material may be a solution that may comprise biosorbable materials, such as poly-(L-lactic acid) (PLLA), poly-(D,L-lactide), and poly glycolic acid (PGA), for example, or other bioabsorbable, non-metallic materials, which may be especially tailored for conferring hardness, tensile strength and compressive strength to the centrifuged core.

In another embodiment, the media material may also comprise a growth material which may contain growth factors such as autogenous growth factors, for example platelet-rich plasma (PRP), optionally in combination with hyaluronic acid (HY acid).

The term "growth factor" as used in the present application is intended to include all factors, such as proteinaceous factors, for example, which play a role in the induction or conduction of growth of bone, ligaments, cartilage or other tissues associated with bone or joints. In particular, these growth factors include bFGF, aFGF, EGF (epidermal growth factor), PDGF (platelet-derived growth factor), IGF (insulin-like growth factor),TGF-β I through III, including the TGF-β superfamily (BMP-1 through 12, GDF 1 through 12, dpp, 60A, BIP, OF).

The growth material may be added to the media material solution to be incorporated into the centrifuged core. Optionally, the growth material may comprise additional osteoconductive bone adhesives, calcium carbonate, fatty acids, lubricants, antiseptic chemicals and/or antibiotics. The additional lubricants and/or the antiseptic and/or the antibiotic will typically be present in the media material solution in a predetermined concentration range, which will be dependent upon the particular recipient site and application, as well as the specific activity of the antiseptic and/or the antibiotic.

If the processing takes place at a remote location (such as a tissue banking facility), an osteochondral core from a graft such as femoral condyle, talus, or humeral head, for example, is first obtained by conventional methods at the tissue banking facility. Prior to storage and delivery to the surgeon, the osteochondral core is placed in the centrifugation system 10 of FIG. 1 to remove blood, lipids, or other potentially antigenic or contaminating materials, and to obtain the centrifuged core. As in the "operating room" method, the centrifuged core may be optionally infused with a media material that reduces the chance of disease transmission and aids in the healing of the recipient site to which the centrifuged core is to be transferred. The media material may be a solution comprising bioabsorbable materials, growth materials, osteoconductive bone adhesives, calcium carbonate, fatty acids, lubricants, antiseptic chemicals and/or antibiotics.

Figure 3:
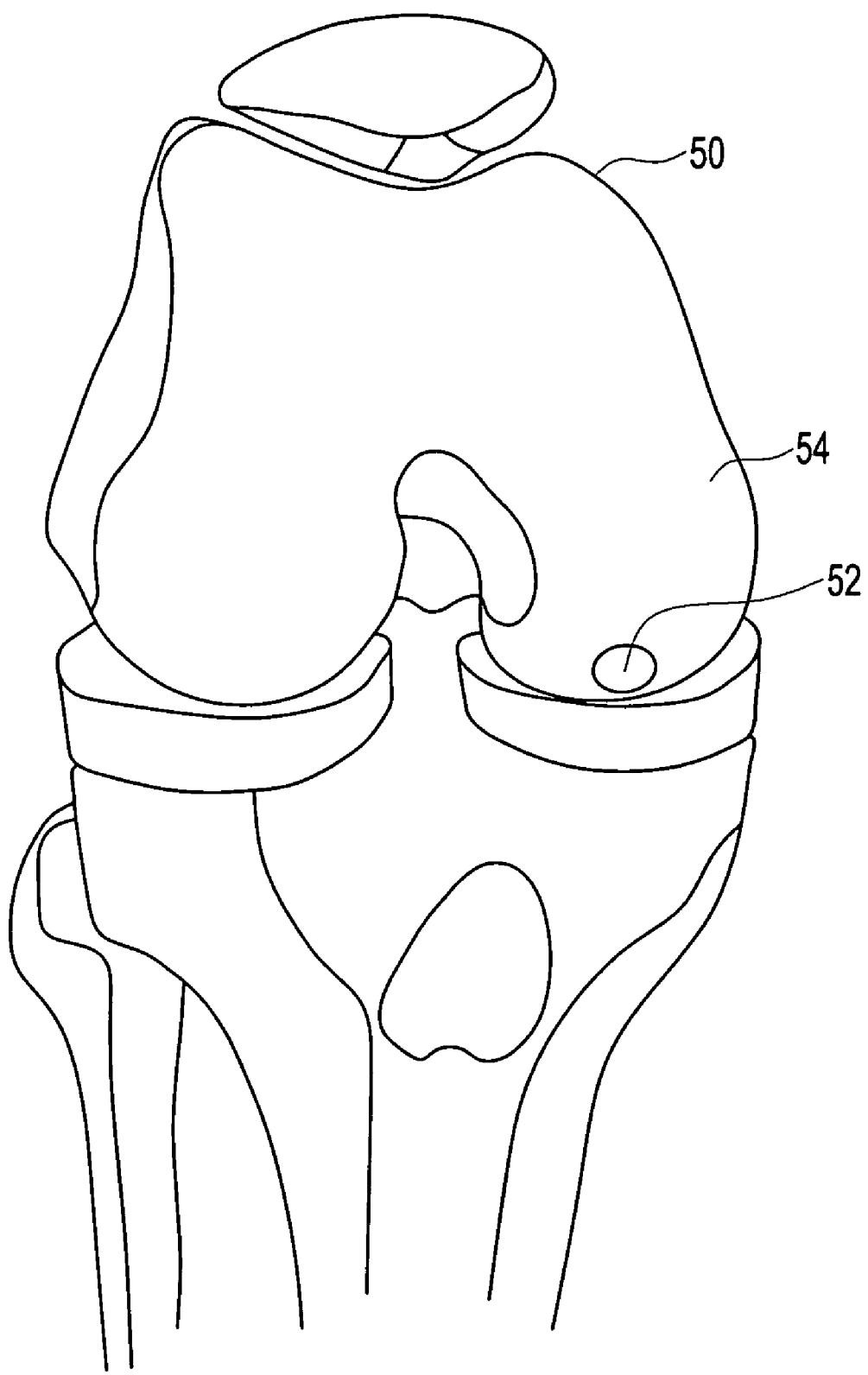
FIG. 3 illustrates a schematic anterior view of a right knee undergoing a method of osteochondral repair using a centrifuged core according to the present invention.
Figure 4:
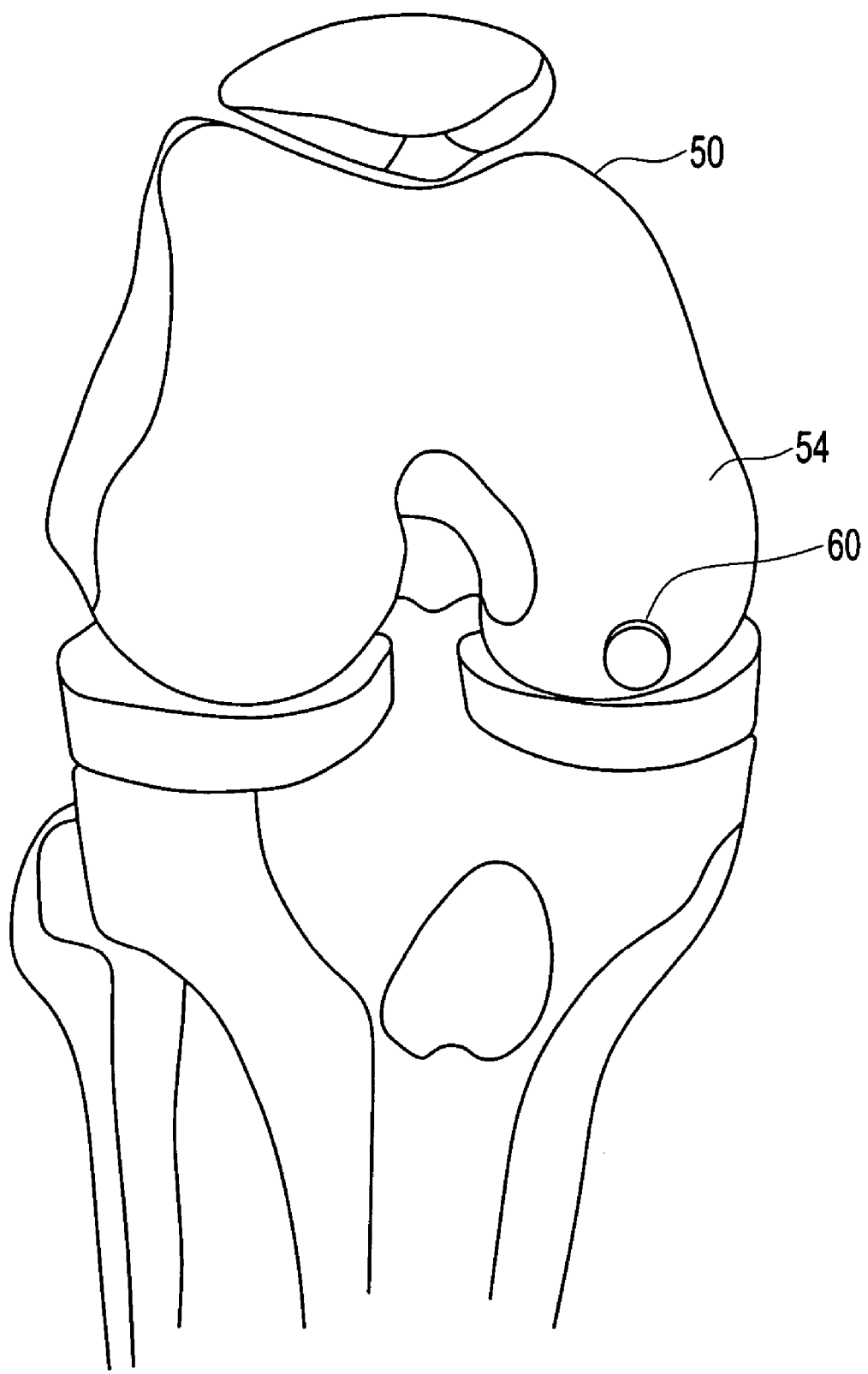
FIG. 4 illustrates the schematic anterior view of the right knee of FIG. 3 at a step subsequent to that of FIG. 3.
Figure 5:
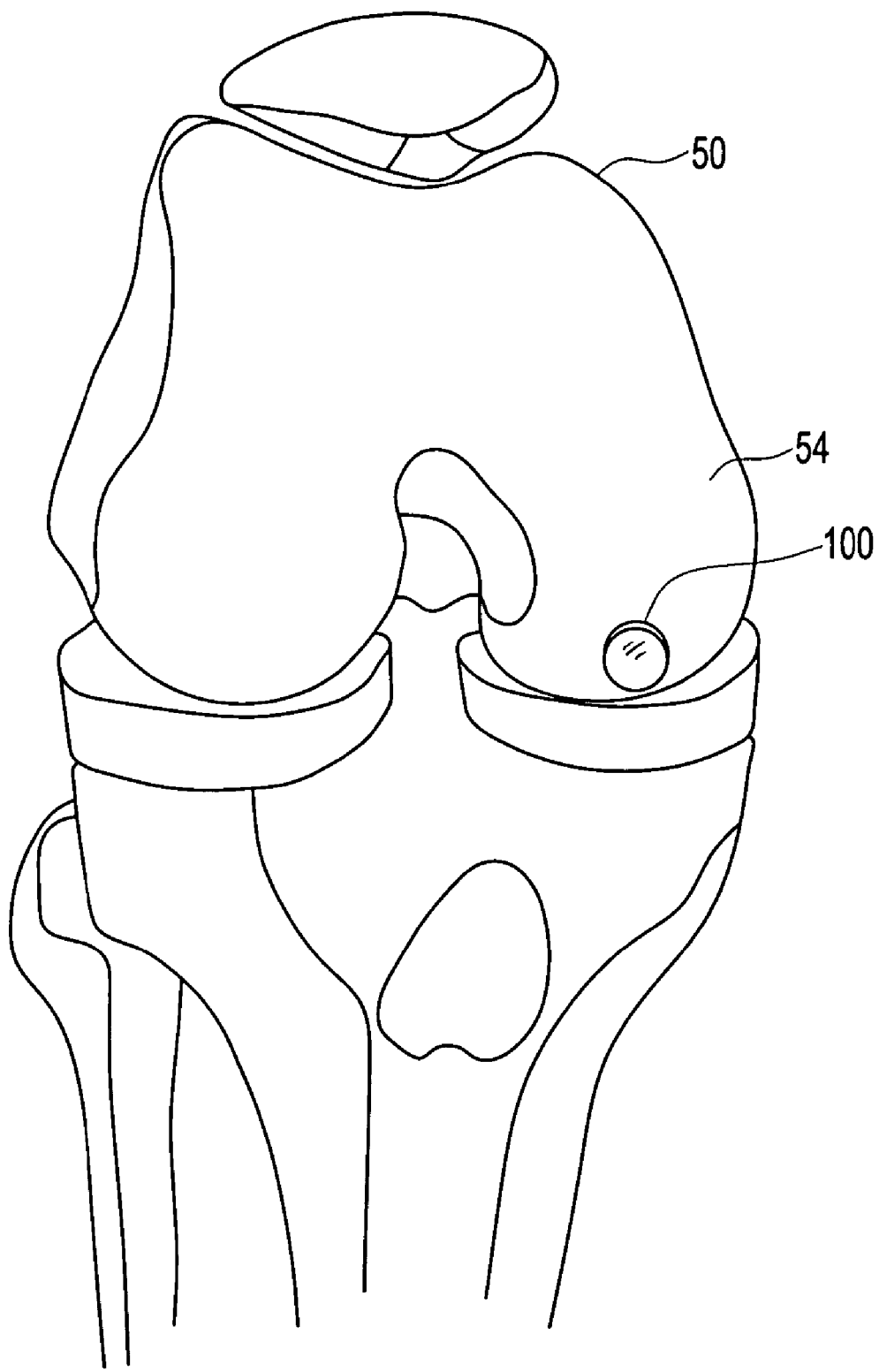
FIG. 5 illustrates the schematic anterior view of the right knee of FIG. 3 at a step subsequent to that of FIG. 4.

The centrifuged core 100 of the present invention may be employed in a variety of osteochondral repairs, for example in osteochondral repairs of damaged articular joint surfaces in femoral condyles or tibial surfaces. FIG. 3 illustrates a schematic anterior view of a right knee 50 with a chondral defect 52 in femoral condyle 54 undergoing a method of osteochondral repair using a preformed centrifuged core according to the present invention. Once recipient socket 60 (FIG. 4) is formed by known methods in the art, the centrifuged core 100 selected to fit the recipient socket 60 is inserted into the recipient socket, as shown in FIG. 5. As described above, the centrifuged core 100 may be formed by employing the centrifugation system 10 either in the operating room or at a remote location (for example, a tissue banking facility). Optionally, the centrifuged core 100 may be also infused with, or subjected to, various growth factors such as autogenous growth factors, hyaluronic acid (HY acid), antiseptics, antibiotics, osteoconductive bone adhesives, calcium carbonate, fatty acids and lubricants, or to combinations of these materials.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method of osteochondral repair, comprising the steps of:
   creating a recipient socket in bone;
   removing an osteochondral core from a graft, the osteochondral core being configured to fit the recipient socket;
   placing the osteochondral core in a centrifuge system and subjecting the core to centrifugation to obtain a centrifuged core;
   subjecting the centrifuged osteochondral core to a solution comprising autogenous growth factors; and
   inserting the centrifuged core into the recipient socket.

2. The method of claim 1, further comprising the step of subjecting the centrifuged core to a solution comprising a material selected from the group consisting of bioabsorbable materials, hyaluronic acid, antiseptics and antibiotics.

3. The method of claim 1, wherein the osteochondral core is removed from the graft and centrifuged in an operating room wherein the osteochondral repair takes place or is scheduled to take place.

4. The method of claim 1, wherein the osteochondral core is created and centrifuged in an area remote from an operating room wherein the osteochondral repair is scheduled to take place.

5. A method of conducting osteochondral repair, the method comprising the steps of:
   removing an osteochondral core from a graft in an operating room, the osteochondral core being configured to fit a bone socket;
   placing the osteochondral core in a centrifuge in the operating room;
   subjecting the osteochondral core to at least one rotational movement to obtain a centrifuged osteochondral core in the operating room;
   subjecting the centrifuged osteochondral core to a solution comprising autogenous growth factors; and
   inserting the centrifuged osteochondral core into the bone socket in the operating room.

6. The method of claim 5, further comprising the step of subjecting the centrifuged osteochondral core to a solution comprising a material selected from the group consisting of bioabsorbable materials, hyaluronic acid, antiseptics, antibiotics, osteoconductive bone adhesives, calcium carbonate, fatty acids and lubricants.

7. A method of conducting osteochondral repair, the method comprising the steps of:
   removing an osteochondral core from a graft in a remote location that is different from an operating room, the osteochondral core being configured to fit a bone socket;
   placing the osteochondral core in a centrifuge in the remote location;

subjecting the osteochondral core to at least one rotation to obtain a centrifuged osteochondral core in the remote location;
subjecting the centrifuged osteochondral core to a solution comprising autogenous growth factors;
delivering the centrifuged osteochondral core to the operating room; and
inserting the centrifuged osteochondral core into the bone socket in the operating room.

8. The method of claim 7, further comprising the step of subjecting the centrifuged osteochondral core to a solution comprising a material selected from the group consisting of bioabsorbable materials, hyaluronic acid, antiseptics, antibiotics, osteoconductive bone adhesives, calcium carbonate, fatty acids and lubricants.

9. The method of claim 1, wherein the osteochondral core is from the femoral condyle, talus or humeral head.

10. The method of claim 5, wherein the osteochondral core is from the femoral condyle, talus or humeral head.

11. The method of claim 7, wherein the osteochondral core is from the femoral condyle, talus or humeral head.

* * * * *